United States Patent
Buncke

[19]

[11] Patent Number: 5,931,855
[45] Date of Patent: Aug. 3, 1999

[54] SURGICAL METHODS USING ONE-WAY SUTURE

[75] Inventor: Harry J. Buncke, Hillsborough, Calif.

[73] Assignee: Frank Hoffman, Hillsborough, Calif.; a part interest

[21] Appl. No.: 08/859,887

[22] Filed: May 21, 1997

[51] Int. Cl.$^6$ ................................................ A61B 17/04
[52] U.S. Cl. ........................ 606/228; 606/215; 606/224; 606/216
[58] Field of Search ................................. 606/224–228, 606/215–216

[56] References Cited

U.S. PATENT DOCUMENTS

| | | | |
|---|---|---|---|
| 3,123,077 | 3/1964 | Alcamo | 606/224 |
| 5,123,913 | 6/1992 | Wilk et al. | 606/232 |
| 5,222,976 | 6/1993 | Yoon | 606/223 |
| 5,425,746 | 6/1995 | Proto et al. | 606/224 |
| 5,425,747 | 6/1995 | Brotz | 606/224 |
| 5,450,860 | 9/1995 | O'Connor | 128/898 |
| 5,584,859 | 12/1996 | Brotz | 606/224 |

OTHER PUBLICATIONS

H. Han, et al. "Mating and Piercing Micromechanical Structures for Surface Bonding Applications".
Micro ElectroMechanical Systems (MEMS–91), Jan. 31—Feb. 2, 1991, CH2957–Sep. 1991, pp. 253–258, 1991.

H. Buncke, et al. "The Suture Repair of One–Millimeter Vessels". Micro–Vascular Surgery, pp. 24–35 (esp. p. 34), 1966.

*Primary Examiner*—Gary Jackson
*Attorney, Agent, or Firm*—Thomas M. Freiburger

[57] ABSTRACT

Methods are disclosed for binding together human or animal tissue using one-way sutures having barbs on their exterior surfaces, allowing passage of a needle-drawn suture in one direction through tissue, but not in the opposite direction. In closing a wound, the sutures are passed through tissue at each of the opposed sides of the wound, forming suture pairs in which trailing ends of the sutures are juxtaposed in the wound. The number of suture pairs is selected in accordance with the size of the wound. The wound is closed and ends of the sutures of each suture pair are secured together, which may be by heat bonding or surgical knots. In a variation of this procedure double-armed sutures are used. In another variation detachable needles are used to leave the barbed sutures below the skin. The invention avoids loop stitching, minimizing scarring. In addition to wounds at the skin surface, the method is useful in binding together severed tendons or other internal tissue of a patient, providing considerable tensile strength with a minimum of suturing and locating the tensile support precisely where needed. In facelifts and other cosmetic operations, the sutures are used to provide lines of tissue support beneath the skin.

27 Claims, 9 Drawing Sheets

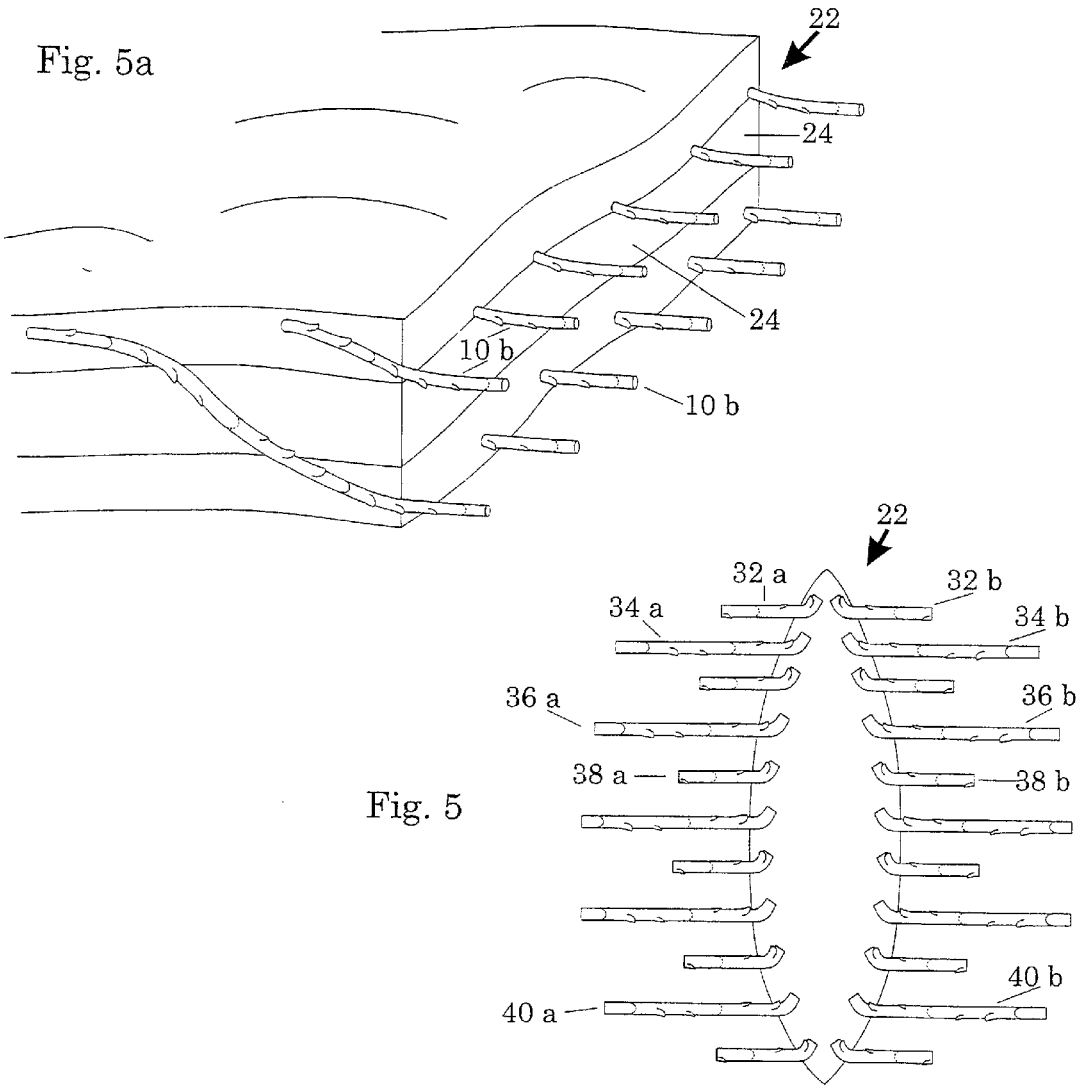
Fig. 5a
Fig. 5
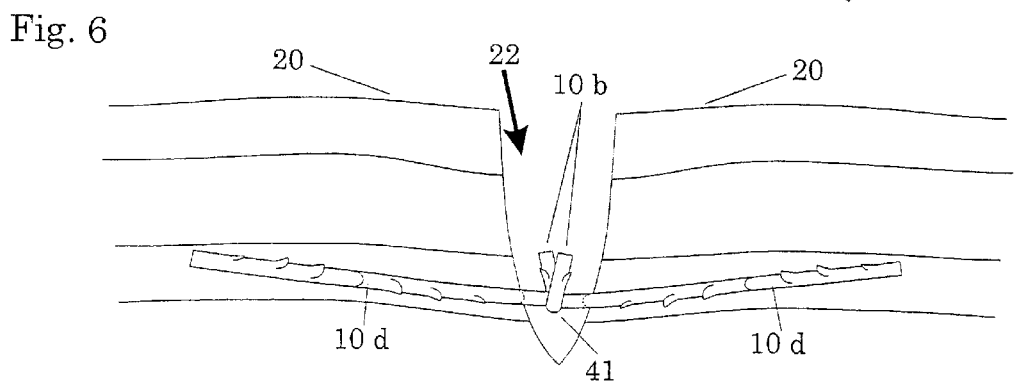
Fig. 6

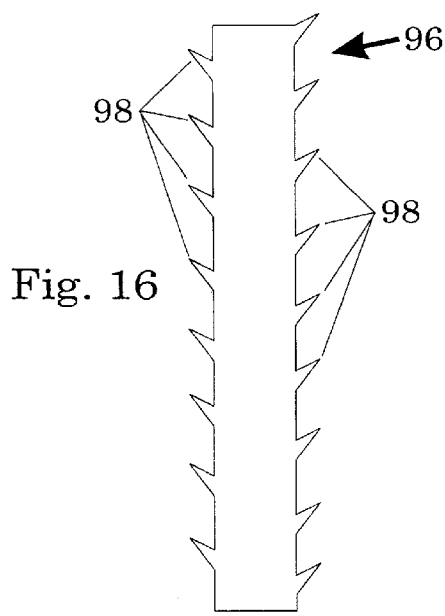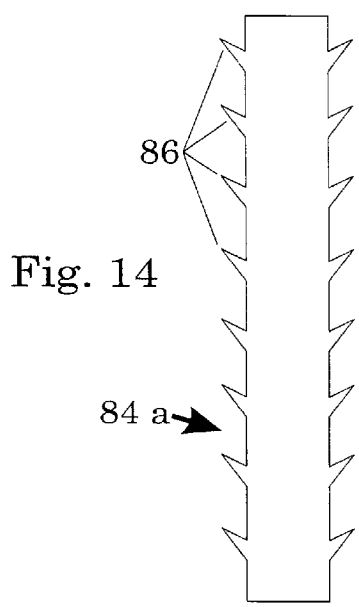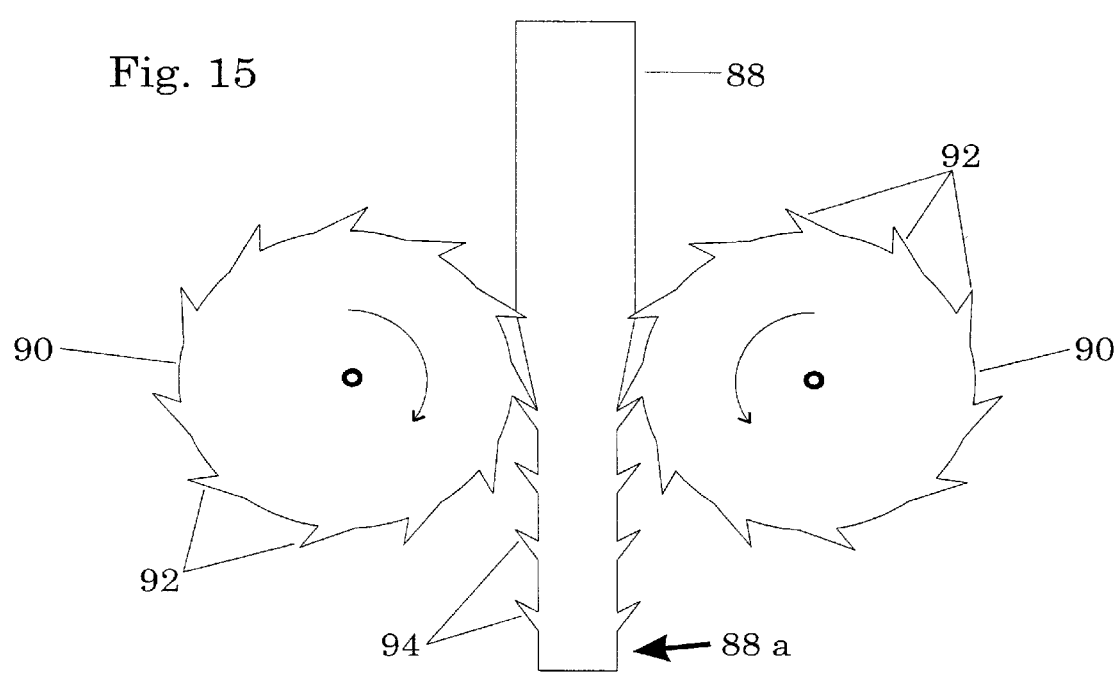

Fig. 17
Fig. 18
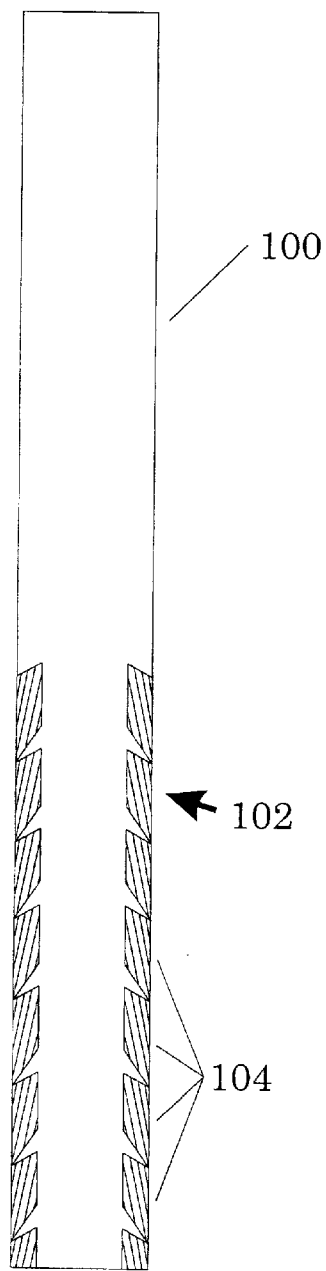
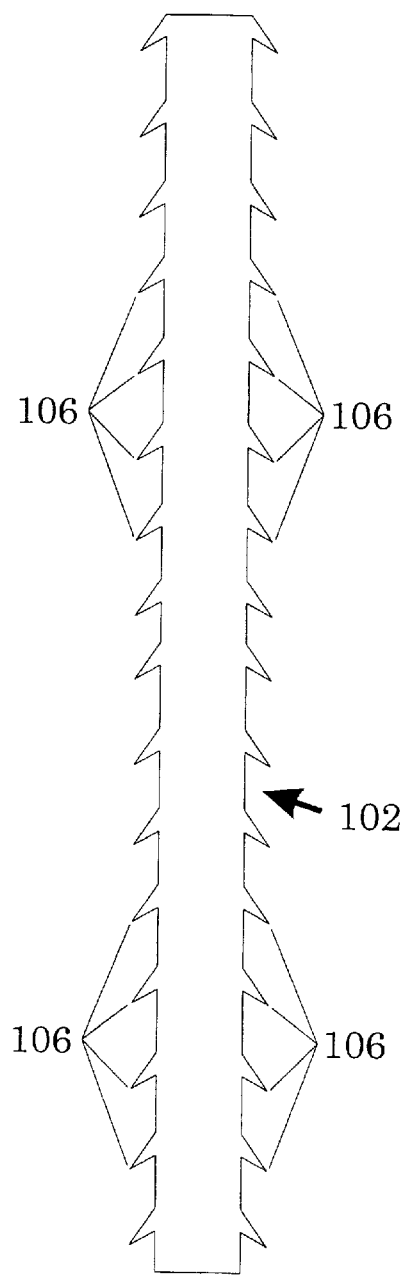

SURGICAL METHODS USING ONE-WAY SUTURE

BACKGROUND OF THE INVENTION

The invention concerns surgical procedures, and in particular relates to surgical methods using a one-way suture which has barb elements enabling the suture to be pulled through tissue in one direction, but resisting movement in the opposite direction. The methods include closing wounds, tissue support and repair of internal tissues such as tendons and ligaments.

Sutures have been used in surgical procedures to close surgical and traumatic wounds, to close the skin in plastic surgery, to secure damaged or severed tendons, muscles or other internal tissues, and in microsurgery on nerves and blood vessels, all for holding tissues together to support healing and regrowth. Such sutures are attached to the shank end or trailing end of a needle. The sutures can be a monofilament or a braided material and many are available as a one-piece unit pre-attached to a needle. Sutures can be of non-absorbable material such as silk, nylon, polyester, polypropylene or cotton, or of bioabsorbable material such as polymers and copolymers of glycolic and lactic acid. Loop stitching has been the primary procedure, particularly to close a surface wound, whether an accidental or surgical wound. Such looped sutures, which are similar to the simplest method of seaming two pieces of fabric together, can leave ugly scars and a "Frankenstein" look to the fully healed wound. Although this can be alleviated in some cases and to some extent by using very fine suture material (e.g. 100 microns in diameter), the loop stitching still can cause very visible scars, and for adequate closure of some wounds the suture material must be of a high tensile strength and thus a larger diameter, increasing scarring.

Surface adhesive tapes are often used on the skin to hold small wounds closed to permit healing, but these have relatively low tensile strength and are not useful in many situations. Another approach, sometimes practical, has been the use of staples for holding closed a wound for healing. The staples have relatively high strength and save time, but are not as accurate as sutures, are bulky and painful to remove.

Surgical sutures having barbs, for providing a non-slip attribute in one direction, are shown in U.S. Pat. No. 3,123,077. In addition, in about the 1960s a metal tendon suture was produced and tried, the suture having a single, large barb for gripping of the tendon tissue. The metal suture was not successful and may no longer be available, and the technique is outdated.

U.S. Pat. Nos. 5,425,747 and 5,584,859 disclose a type of "suture" having external barbs for holding together the two sides of an open wound. Although the theory of operation of the suture devices of these two patents is similar to that of the present invention, these prior suture devices were in essence a single relatively rigid frame. the disclosed devices had "lateral members" with barbs, the lateral members being shaped somewhat like small spears which were to be inserted into the tissue on opposite sides of a wound, to bind the wound together. The arrays of barbed, parallel-extending spears on both sides of the wound were held together by a "central body member" which lay within the wound and parallel to the length of the wound and which was secured to the barbed spears on each of the two sides. All of these components were described as being of bioabsorbable material. In the '859 patent, stretchable elastic connectors secured the spear-like lateral members to the central body member, so as to impose a tension force to pull the two sides of the wound together.

The spear-like barbed lateral members of the two described patents were required to be pushed into the patient's tissue, and therefore had to be of sufficient stiffness and large enough diameter such as to be capable of being pushed into the tissue. The resulting tissue securement would appear to be bulky and painful. The larger foreign body would tend to cause excessive scarring and would tend to increase the possibility for wound infections.

It is an object of the present invention to improve on suturing techniques for closing wounds and severed tissues, and for performing cosmetic surgery such as face lifts, while minimizing scarring and providing a strong retaining force between the two side of tissue.

SUMMARY OF THE INVENTION

The invention described herein includes several surgical procedures for binding together living tissue using one-way sutures having barbs on their exterior surfaces and a needle on one or both ends. The one-way sutures allow passage of a needle-drawn suture in one direction through tissue but not in the opposite direction, thus having the capability to put tension in the tissue when tension is placed on the trailing end of the suture.

In a procedure for closing a wound or surgical incision, the one-way sutures are passed through tissue at each of the opposed sides of the wound, forming suture pairs in which trailing ends of the sutures are positioned generally in alignment at opposite sides of the wound. On insertion of each suture, the needle is pushed to extend out of the flesh at a point laterally remote from the wound, then the needle is pulled out to draw the suture to the desired position, and the suture is severed from the needle. The number of suture pairs is chosen in accordance with the size of the wound and the strength required to hold the wound closed.

Once all sutures are in place, the wound is closed (as by holding or clamping), and ends of the sutures of each suture pair are secured together, and this may be by heat bonding or surgical knots.

By the described method of using one-way sutures to hold closed a wound, loop stitching is avoided and scarring is minimized.

In addition to closing wounds at the skin surface, the method of the invention is useful in binding together partially or completely severed tendons or other internal tissue of a patient or animal, providing considerable tensile strength with a minimum of suturing. The procedure locates the tensile support precisely where it is needed.

In facelifts and other cosmetic operations, the surgeon uses the one-way sutures to provide lines of tissue support beneath the skin.

In the procedures of the invention, the sutures are hidden and may be left in place. If desired, however, they may be formed of bioabsorbable material.

In a variation of the above procedure, double-armed sutures are used, with first and second surgical needles oriented in opposite directions and a single suture extending between the shank ends of the two needles. The suture has exterior barbs oriented in one direction for about half the length of the suture and in the opposite direction for the other half of the suture, each portion having the barbs oriented so as to allow movement along with the adjacent needle secured to the suture. In the double-armed suture procedure, the surgeon may fully insert one side of the suture at one side of the wound or severed tissue, then manually close the wound as he draws the opposite needle through the tissue to draw into place the other side of the suture, thus closing the wound as the double-armed suture is fully secured in position. Both needles are severed from the sutures at the points of exit from the tissue.

In another variation of the procedure, the surgeon can use a pull-away needle which is detachable from the one-way suture when the needle is pulled with sufficient tension. This enables the surgeon to leave the barbed suture well below the skin, avoiding "puckering" of the skin from the pull of the barbed suture just below the skin surface. This can be done with double-armed sutures as well.

In a facelift operation, the surgeon selects one or more paths through the patient's tissue where lines of tissue support are needed. The surgeon selects a surgical needle of sufficient length to be inserted through one of the selected paths in the tissue, the needle having a shank end secured to a one-way suture with exterior barbs providing for gripping of the tissue in one direction only, the direction opposite that in which the needle is pushed through the tissue. The surgeon inserts the needle into the tissue, below the skin and along the selected path for the desired line of tissue support, until the needle extends out through the skin at a distal end of the selected path. Then the surgeon grips the needle from the point end and pulls it out of the tissue, leaving the one-way suture lying within the tissue along the selected path. The suture is then severed from the surgical needle, at a point below the skin, leaving the leading end of the one-way suture hidden beneath the skin at that distal end.

The surgeon repeats the above procedure for additional lines of tissue support, as needed for the particular facelift operation. Once all one-way sutures are in place along the desired lines of tissue support, the surgeon applies tension to the trailing end of each suture, such tension being in a direction opposite the direction in which the needle was drawn, to engage the barbs against the internal tissue along the desired lines of tissue support. The trailing end of each suture is secured in such a way that the desired line of support is placed in tension. The trailing end of each suture may be secured to the patient's adjacent tissue, or to another one-way suture which extends in essentially an opposite direction, or a double armed opposing barbed suture can be used.

Accordingly, it is among the objects of the described invention to provide an efficient procedure for closing wounds, incisions and severed tissue such as tendons, joint capsules and ligaments, as well as to establish a highly efficient and invisible tissue support procedure, especially for facelift operations. These and other objects, advantages and features of the invention will be apparent from the following description of preferred embodiments, considered along with the accompanying drawings.

DESCRIPTION OF THE DRAWINGS

FIG. 5 is a schematic perspective view indicating a series of one-way sutures inserted at one side of a wound, at different levels.

FIG. 5A is a plan view showing the patient's skin with the wound still open, and showing a series of opposed suture pairs which have been put in place by the procedure shown in FIGS. 2–4.

FIG. 6 is a cross sectional view similar to FIG. 4, but with the wound closed and showing a knot being tied to join trailing ends of a sutured pair.

FIGS. 13–18 are views showing schematically several different techniques for production of the one-way sutures.

DESCRIPTION OF PREFERRED EMBODIMENTS

Figure 1:
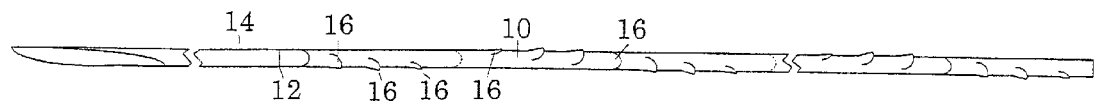
FIG. 1 is a view showing a surgical needle with a one-way suture secured to the shank end of the needle, the suture including barbs on its exterior surface.

FIG. 1 shows schematically a suture 10 secured to the trailing end 12 of a surgical needle 14 in accordance with the invention. As described above, the suture 10 is a one-way suture, allowing its travel through tissue in one direction only, toward the left as viewed in FIG. 1, due to the presence of a multiplicity of barbs 16 on the exterior surface of the suture. The barbs 16 are configured to engage against a patient's tissue, much in the manner of a bee's stinger or a porcupine's quill. The surgical needle 14 is long enough to serve the type of tissue repair to be addressed, so that the needle can be completely removed, leaving the suture in the desired position within the tissue.

Figure 1A:
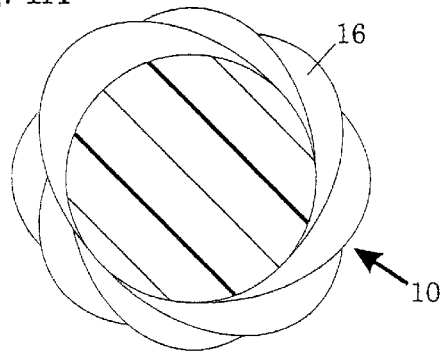
FIG. 1A is a cross sectional view showing the suture of FIG. 1.

FIG. 1A shows in cross section an example of one type of barb configuration which can be used on the sutures of the invention. The suture 10, which may be about 100 to 500 microns in diameter, has the barbs 16 formed in a helical pattern; however, the barbs can also be formed in other patterns and by various means, as explained below.

Figure 2:
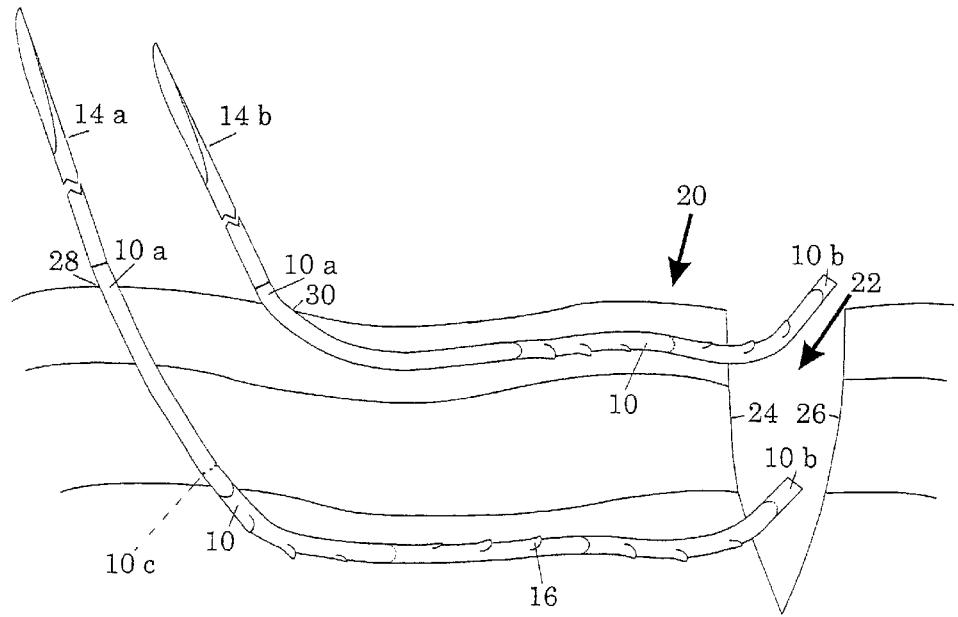
FIG. 2 is a cross sectional view showing a portion of a patient's skin and subcutaneous tissue, with a surgical wound or incision from the skin surface down into the tissue, and showing the use of the needle and one-way suture of FIG. 1.

FIG. 2 indicates schematically a cross section of a patient's tissue 20, showing an open wound or surgical incision 22 with sides 24 and 26. The figure shows surgical needles 14a and 14b which have drawn one-way sutures 10 through the tissue, to points 28, 30 of exit from the skin. The barbed, one-way sutures 10 remain in the tissue, at desired locations (at two different levels in the wound, in this example), with trailing ends 10b of the sutures left extending into the wound 22. Again, the needles 14a and 14b are selected to be sufficiently long to extend through the entire path where the sutures 10 are to be placed.

In all cases the leading ends 10a of the sutures will be cut off so as to lie below the surface of the skin, which is easily accomplished by depressing the skin immediately around the suture and severing the suture closely against the skin, with the trailing end of the suture tensioned, then allowing the skin to cover the end of the suture. However, in many cases it is important that the skin surface not "pucker" inwardly due to tension in the suture just below the skin. This potential problem can be addressed in several ways. One procedure is to provide, and to select, the proper needle and suture combination for the particular situation to be addressed, such that the leading end 10a of the suture will be free of barbs in an initial region, for a selected distance. In FIG. 2 one of the sutures 10 is shown with a dotted line 10c indicating a location where the barbs 16 commence, continuing toward the trailing end 10b of the suture. Thus, the region between the leading end 10a and the dashed line 10c is free of barbs, so that no tension is exerted in the tissue to pull downwardly on the skin. Another method for avoiding this potential problem, and under many circumstances the best method, is to use a pull-away needle/suture combination, in which the needle is detachable from the leading end of the suture when sufficient force is applied. One such system is marketed as De-tach by Davis and Geck. The De-tach needle requires a pulling force equal to about one-third the tensile strength of the suture itself, to pull the needle free of the suture. Such a detachable arrangement can easily be made with the barbed sutures of the invention, such as by swaging a metal end of the needle over the leading end of the suture with just sufficient force to allow the suture to be pulled through tissue but still allowing the needle to be pulled free when deliberate force is applied. To use such a detachable needle system, the surgeon simply holds the trailing end 10b of the suture after the suture has been emplaced and pulls the needle with the force required to detach it.

One aspect of the invention is that the detachable needle preferably has at its base end length markings, e.g., at one centimeter intervals from the trailing end of the needle, to show the surgeon how far the suture end lies beneath the skin. With reference to such markings the surgeon can gauge the depth of the suture, predetermining the depth of needle-suture separation.

Figure 3:
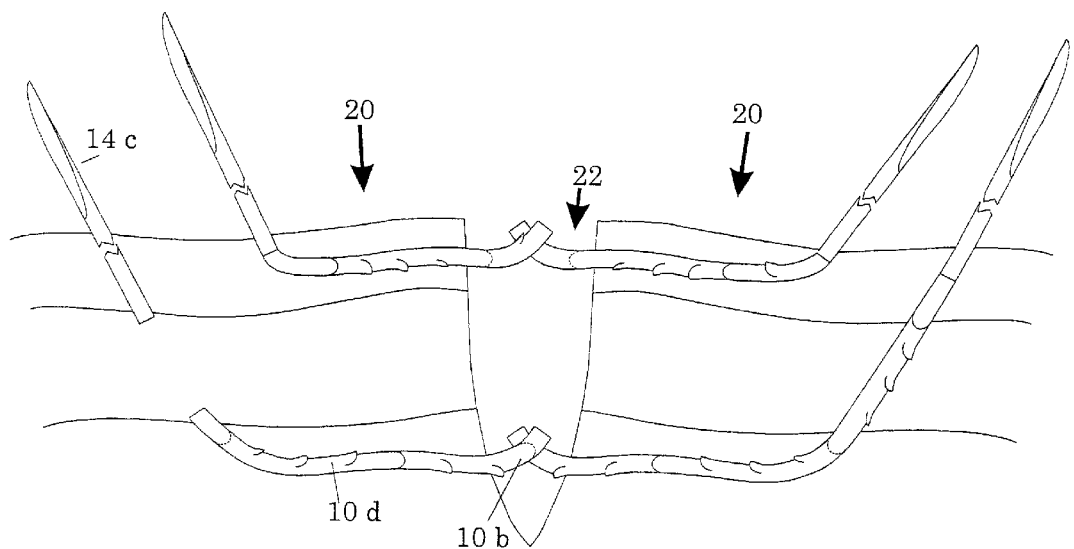
FIG. 3 is a cross sectional view of patient tissue similar to FIG. 2, but showing use of a needle and suture at both sides of the wound or incision and showing an alternate method for removing the needle from the suture below the skin.
Figure 3:
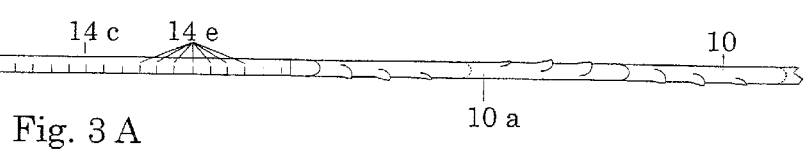

FIG. 3 gives a schematic indication of this procedure. A suture 10d which has been inserted at a lower level in the patient's tissue 20, from near the bottom of a wound 22, has been detached from a needle 14c by pulling the leading end of the needle 14c firmly while holding the trailing end 10b of the implanted suture. As a result of this procedure, the surgeon can select a shorter suture than otherwise needed, can place the suture 10d in a more horizontal or skin-parallel position, correctly aligned with the desired tension to close the wound 22, and the leading end of the suture need not be brought through or even close to the skin surface. In addition, there is no need for a selection of needles/suture combinations with different lengths of barb-free "blank" regions behind the needle, as discussed relative to FIG. 2.

The sutures in FIG. 3 other than the suture 10d are not shown as having been placed with detachable needles, since the figure is meant to illustrate different techniques. Normally, but not necessarily, the same procedure would be used for all procedures around a particular wound.

FIG. 3A shows a detachable needle 14c, with distance markings 14e at the base end of the needle. The needle 14c is detachably secured to the leading end 10a of a one-way suture 10.

Figure 4:
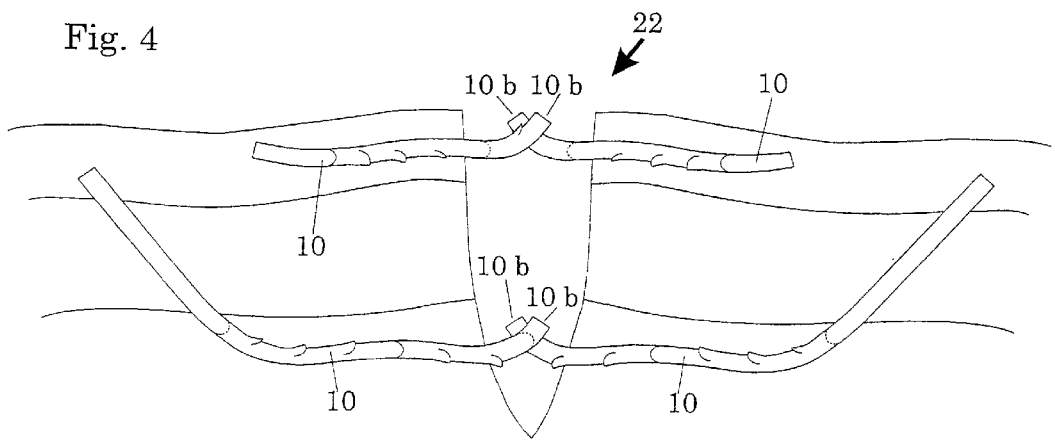
FIG. 4 is another cross sectional view similar to FIG. 2, but with the surgical needles removed and sutures severed from the needles below the skin surface and with trailing ends of the sutures extending into the open wound.

FIGS. 3 and 4 show two different stages in the procedure using the one-way sutures of the invention. FIG. 3 shows that the sutures are emplaced in pairs, so that corresponding juxtaposed sutures can be attached when the wound is to be closed, and FIG. 4 shows the sutures, in place under the skin, after removal of the needles. Once all suture pairs have been put in place, the trailing ends of the sutures will be ready for attachment together with the wound 22 held closed.

FIG. 5 shows schematically, in plan view, series of suture pairs, each pair having sutures implanted in opposite sides of the wound 22. FIG. 5 shows suture pairs 32a, 32b; 34a, 34b; 36a, 36b; 38a, 38b; 40a, 40b, etc. As indicated, any number of suture pairs can be arranged for tying or otherwise securing them together upon closure of the wound, so that the wound is closed successively from one end to the other and held closed by the connected one-way suture pairs, providing for healing without loop suturing at the surface.

FIG. 5A schematically shows in cross section one side of the wound or surgical incision 22, showing trailing ends 10b of sutures extending into the wound, from sutures which have been pulled into position using surgical needles.

FIG. 6 is a schematic view showing in cross section the tying of a pair of trailing ends 10b of sutures 10 which have been placed in the patient's tissue 20. In this case the sutures 10d are shown extending in positions generally parallel to the surface of the skin, drawn into position by detachable needles such as shown and described with reference to FIG. 3. As mentioned above, the advantages of using this type of detachable needle are (1) the suture can be kept more parallel to the skin surface, so that the tension is pulling in the most efficient direction to close the wound; (2) the suture need not come out through the skin, and can be left deep beneath the skin, preventing any "puckering" of the skin; and (3) the suture can be shorter.

In FIG. 6 the suture ends 10b are tied in a knot, as the wound 22 is held closed, and the tying and drawing of the knot tightly can actually help draw the wound closed.

Figure 7:
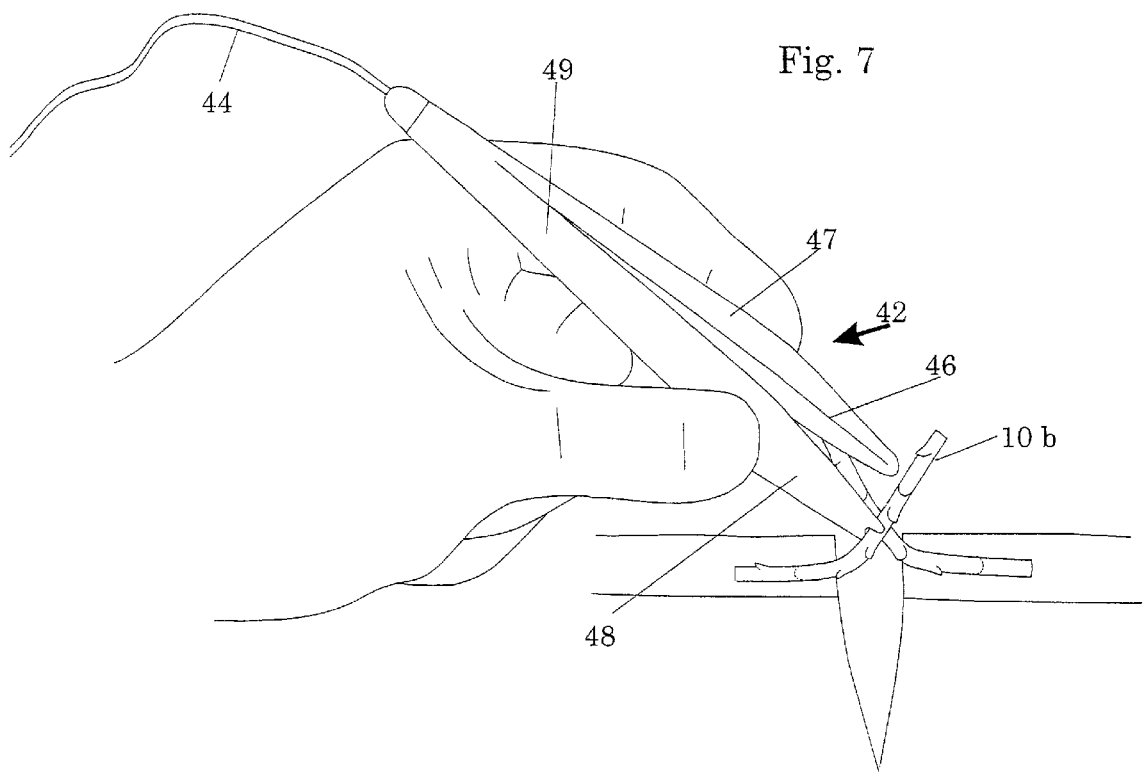
FIG. 7 is a cross sectional view similar to FIG. 6, with the wound closed but with the suture ends being joined by a heat bonding technique.
Figure 8:
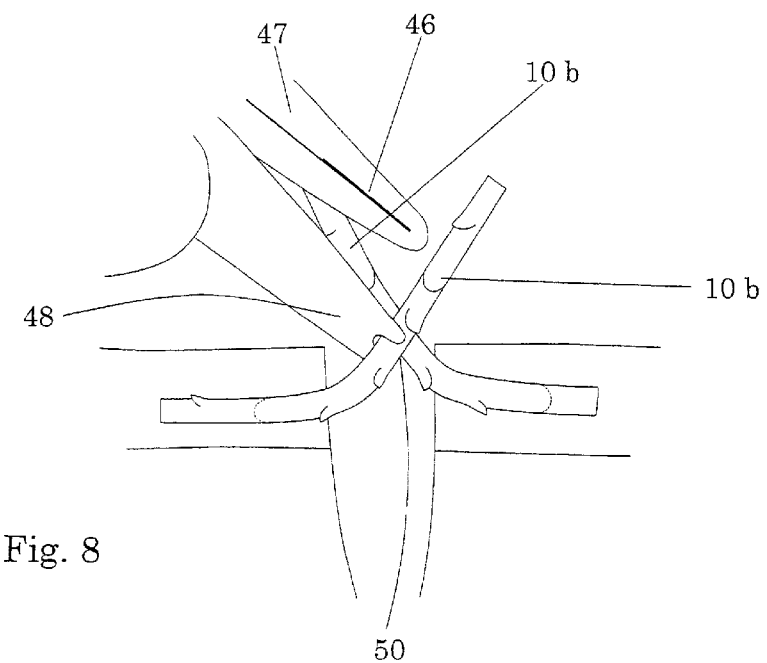
FIG. 8 is an enlarged detail view showing the use of a device for performing the heat bonding of FIG. 7.

However, FIGS. 7 and 8 show an alternative procedure for tying the suture ends together, in which a heat sealing device 42 is used to secure the suture ends together. The device 42 may be shaped generally in the form of a pair of tweezers, with an electrical cord 44 supplying power to an isolated tungsten filament 46 on a first leg 47 of the tool. As can be seen in FIGS. 7 and 8, a metal tip 48 of an opposite leg 49 has a recess or notch 50 which engages the two suture ends 10d. With the two suture ends securely engaged in this notch 50, the two legs of the tweezer-like tool are brought together and the filament 46 contacts the suture ends and simultaneously severs the excess ends of the sutures and bonds the sutures together by fusion. The filament is heated instantaneously by closure of a remote switch. The blade tips 47 and 49 of the instrument act as a heat sink to protect the surrounding tissue.

The surgeon will need to hold or temporarily clamp the wound 22 together while using the heat bonding tool 42. By using the tool 42 the surgeon can quickly bond a series of suture pairs, both shallow and deep pairs, eliminating the surgical knot 41 which is left in the wound by the procedure of FIG. 6.

Figure 9:
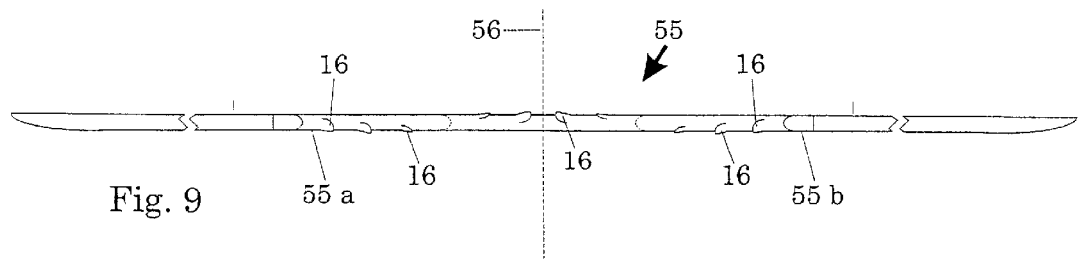
FIG. 9 is a view showing a double-armed suture, with two needles and a barbed suture extending between the needles, the suture having two sections with oppositely-directed barbs.

FIG. 9 shows a double-armed suture 55, similar to the barbed suture 10 described above but having barbs 16 oriented in one direction to one side of a division line 56 and in the opposite direction on the other side. As reviewed earlier, this enables the use of such one-way sutures to close and bind a wound without the need to secure suture ends together in the wound. The double-armed suture 55 of FIG. 9 has a left side 55a and a right side 55b.

Figure 10:
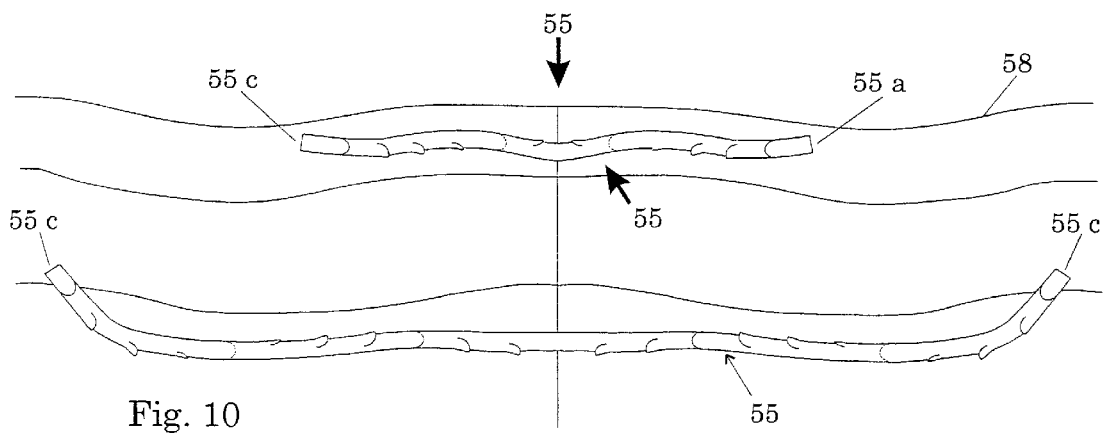
FIG. 10 is a cross sectional view similar to FIGS. 6 and 7 showing a surface wound joined together with a double-armed suture such as shown in FIG. 9, the needles having been removed.

FIG. 10 shows a wound 22 held closed by double-armed sutures 55 according to procedures of the invention. The double-armed sutures 55 have barb reversal points, such as shown at 56 in FIG. 9, located at or close to the closed wound 22, such that the two sides of the double-armed suture each exert tension on tissue at the respective side of the wound. The upper suture 55 in FIG. 10 is shown with cut-off leading ends 55c, which are just below the surface of the skin in accordance with the first form of the invention described above, wherein the sutures are severed at the skin and the skin springs back over the severed ends 55c to cover them. However, the lower double-armed suture 55 shown in FIG. 10 is shown with terminal leading ends 55c which are well down into the tissue, far below the skin surface 58. This is merely for the purpose of illustration and not to suggest that the suturing procedure should be different for the lower suture 55 than for the upper suture 55, although this can be done. The lower suture in FIG. 10 is emplaced by the procedure shown on the lower left in FIG. 3, by a pull-away needle, similar to the De-tach needle/suture combination described above, such that the suture can be drawn more horizontally through the tissue and can be left far below the skin. The patient's tissue is flexible and pliable, and in most cases the surgeon can insert the needle horizontally, then make what is in effect a rather pronounced turn with the needle up toward the surface, by manipulating the skin to angle the needle toward the surface.

The procedure for use of the double-armed sutures 55 is described above, preferably involving first inserting one end of the suture through the tissue to the position desired, with the transition point or barb reversal point 56 located in the wound; then inserting the opposed needle of the double-armed suture into the tissue at the other side of the wound, and drawing this second arm of the suture tight while closing the wound 22, to the closed position shown in FIG. 10. The needles are removed after the suture ends are properly in place.

Figure 11:
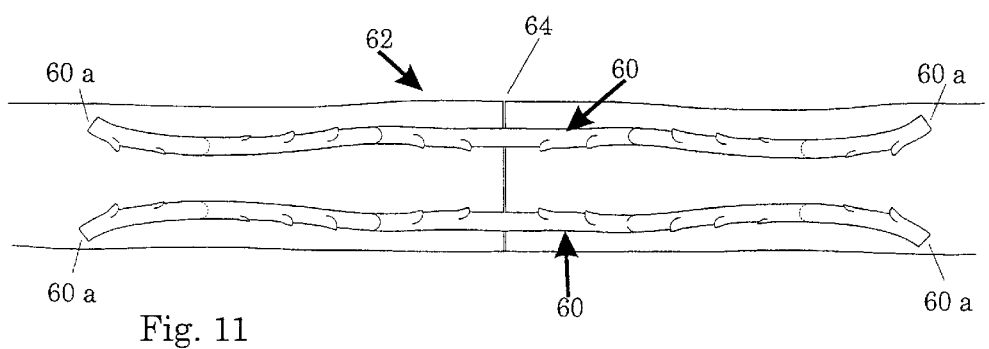
FIG. 11 is a view schematically showing a severed tendon joined together by one-way sutures, which in this case are shown as double-armed barbed sutures.

FIG. 11 shows double-armed sutures 60 used to repair a severed tendon 62. FIG. 11 shows the use of double armed sutures, but the simpler barbed sutures shown in FIGS. 1 through 8 could also be used. In this case there is no concern with "puckering" of the surface, so that the leading ends 60a of the sutures can be simply cut off at the surface of the tendon 62, as generally indicated in the figure. Again, if a double-armed suture 60 is used, the point of barb direction reversal will be located at or very close to the tendon wound 64.

Figure 12:
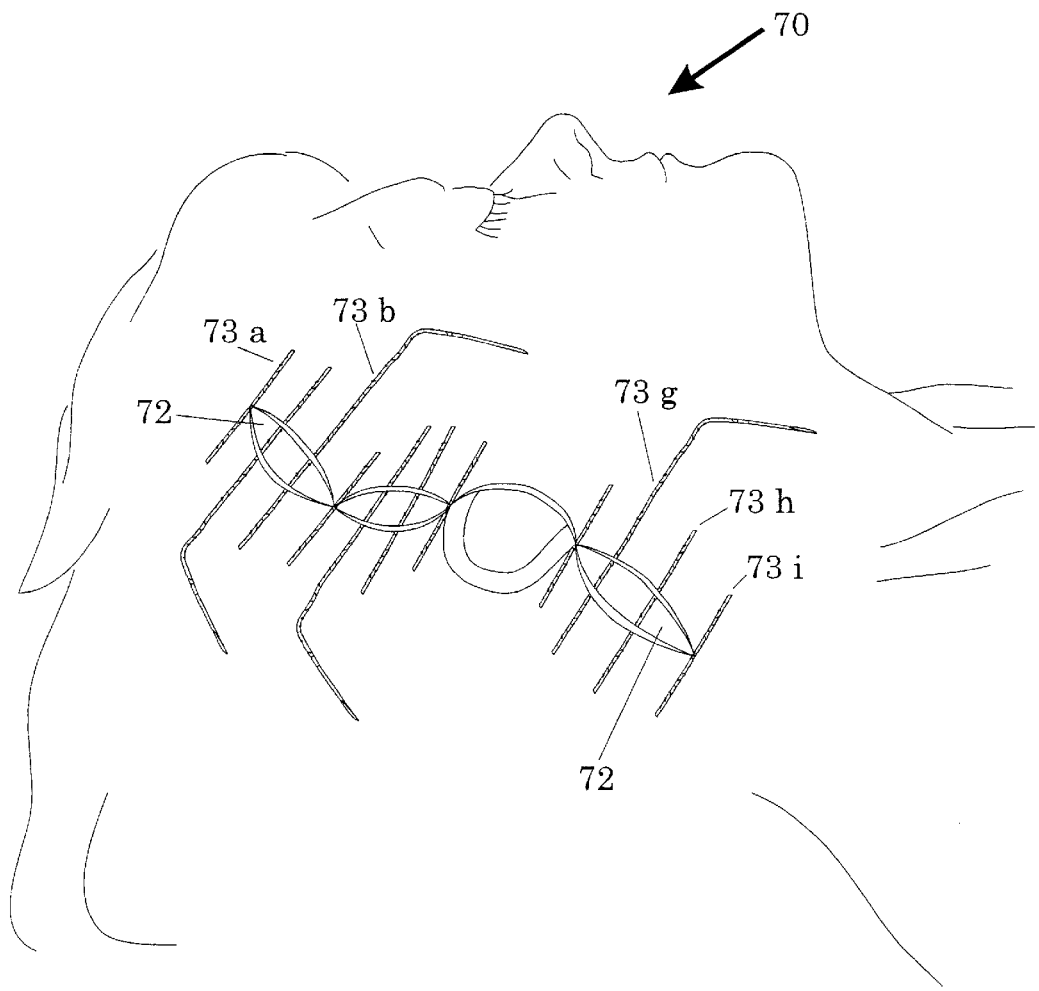
FIG. 12 is a schematic view indicating a facelift procedure using the one-way sutures of the invention.

FIG. 12 is a schematic illustration indicating procedures of the invention in facelift surgery. A facelift patient 70 has a long surgical incision 72, in which skin has been elevated in order to tighten the facial skin, providing tissue support to remove some of the effects of aging. The drawing indicates a series of suture pairs 73a, 73b, . . . 73g, 73h and 73i, which may also be double-armed sutures as described above. As in the surface wound closure situations described and illustrated above, the suture pairs (or double-armed sutures) have barbs for engaging the tissue and gripping the tissue in one direction, so as to pull the tissue toward the surgical wound 72. When each of the suture pairs or double-armed sutures 73a, 73b, etc. has been inserted and the wound has been closed at each suture, the sutures will hold and bind the wound tightly closed, without loop stitching, staples or other means, resulting in reduced scarring. The one-way sutures may be on elongated paths, and the sutures themselves can provide tissue support in the facelift operation, rather than relying solely on the removal of skin at the wound 72 for tightening of the facial tissue. FIG. 12 shows only one example; the one-way sutures of the invention, whether in pairs or alone, can be used in a number of different ways for tissue support. The one-way sutures, inserted along lines beneath the skin, can support the subcutaneous layers better than current procedures.

Figure 13:
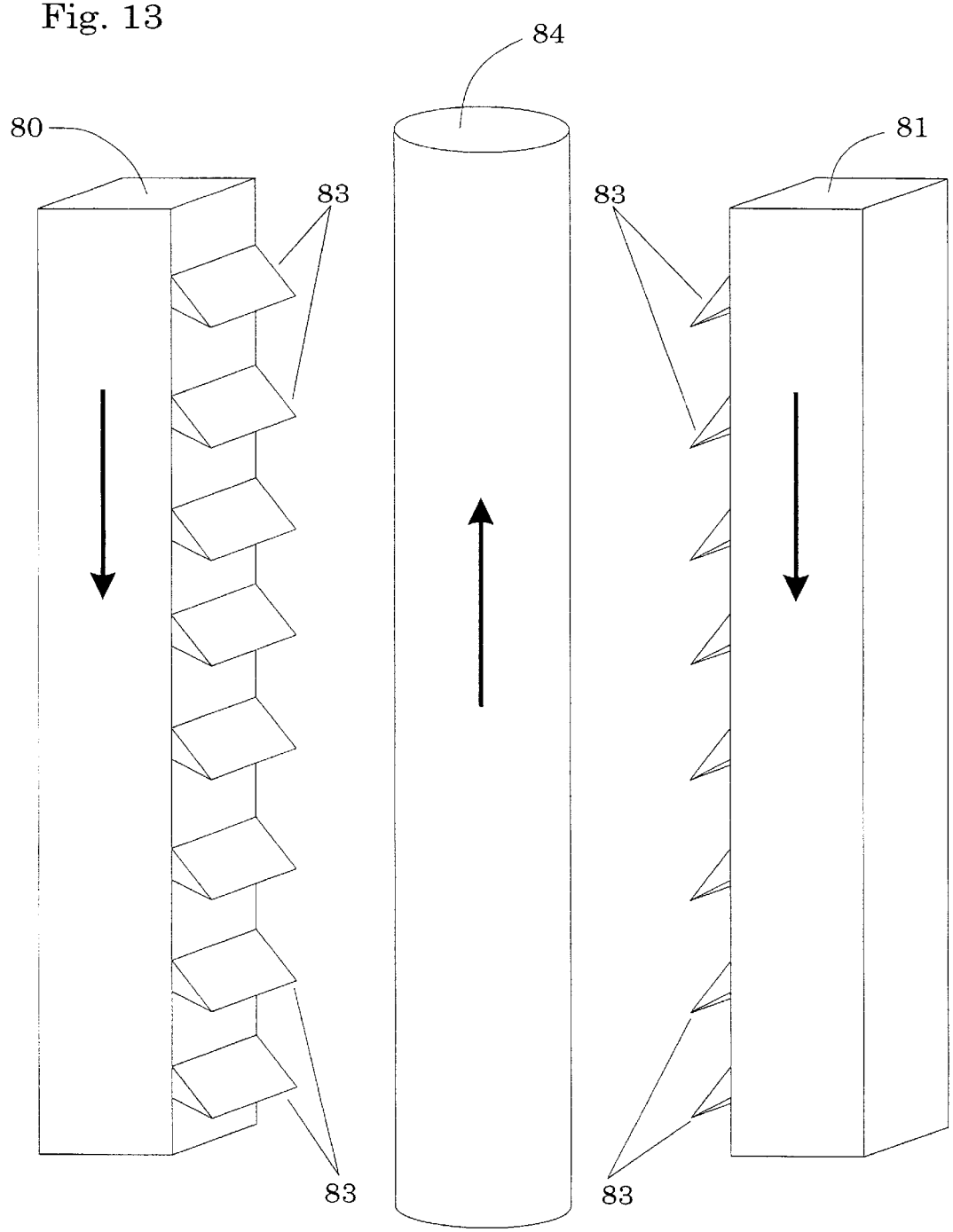

FIG. 13 shows schematically one method for producing one-way sutures for use in the invention. A pair of parallel and movable bars 80, 81 have cutting blades 83 on one surface, the two sets of cutting blades being in facing relationship and being of a size and spacing to form the suture barbs in the size and spacing desired. The cutting blades are precision-formed, since the raw suture 84, which may be nylon or other suitable material, has a small diameter which may be in the range of about 100 to 500 microns. As an example, the barb spacings can be from about 100 microns to about 1 millimeter or even greater. The depth of the barbs formed in the suture material can be about 30 microns to 100 microns, depending, to a large extent, on the diameter of the suture material.

As indicated in FIG. 13, the two bars 80 and 81, with the cutting blades 83, are in a machine which converges them inwardly and downwardly, with reference to the figure, to engage the cutting blades into the exterior walls of the suture filament material 84. The suture material is held stable during this operation, or the suture is advanced upwardly while the bars 80, 81 are moved only inwardly. The distance of relative longitudinal movement between the bars and the suture will determine the depth of the barbs formed, limited by the length of the cutting blades 83 themselves.

FIG. 14 shows a resulting barbed suture 84a as produced by the device shown in FIG. 13. Barbs 86 are closely spaced in the suture 84a, and can be farther apart or in different configurations if desired. As the figure indicates, the barbs 86 are on opposite sides of the suture due to the method of their formation, and they extend outwardly somewhat on the suture due to the manufacturing process, wherein the cutting blades 83 may be removed from the cuts by simply spreading the two bars 80 and 81 (FIG. 13) outwardly, without longitudinal movement of the suture material 84.

FIG. 15 schematically indicates another method for forming a barbed suture 88a from suture filament material 88 such as nylon (or other suitable materials, including resorbable materials as discussed above). This method is somewhat similar to that of FIG. 13, but with rotating cutting wheels 90. These cutting wheels 90 may have cutting blades 92 somewhat similar to the cutting blades 83 shown in FIG. 13. In this production method, the nylon suture material 88 is held with sufficient tension to cause the blades 92 of the wheels 90 to cut into the nylon, forming the barbs 94. The suture being formed nonetheless advances with the motion of the opposed cutting wheels 90, against the imposed resistance. Again, when the cutting blades 92 are pulled free from the formed barbs 94, this pulls outwardly on each barb and causes the barb to protrude slightly from the body of the suture, setting the barbs up for better engagement with the tissue during use.

FIG. 16 indicates a barbed suture 96 having barbs 98 in staggered positions. Such a suture may be formed by a method generally similar to what is shown in FIGS. 13 and 15, but with cutting blades staggered as to height and in different positions around the periphery of the suture material.

FIGS. 17 and 18 indicate another system for producing barbed sutures in accordance with the invention. FIG. 17 shows a raw suture filament 100, which may be about 100 to 500 microns in diameter, being cut into a barbed suture 102 by laser machining. As schematically indicated, a laser beam is directed at the cross hatched areas 104 in FIG. 17, removing these sections to produce barbs 106 as shown in FIG. 18. The barbs can be on opposed sides of the suture, as shown, and staggered if desired. Further, they can be positioned in a spiral pattern if desired, as by rotating the suture filament 100 or moving the laser around the filament, during the material removal operation. Industrial lasers are capable of being focused very sharply, easily down to the range required for this laser machining operation.

Procedures described herein are useful in animal suturing as well as human, and the term "patient" as used in the claims should be taken as including application to animals.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A method for bringing together and holding closed an open wound in human or animal flesh to allow healing and regrowth together of the two sides of the wound, comprising:

(a) in the open wound, inserting a surgical needle into flesh at one side of the wound, penetrating into the flesh wall at the one side, the needle having a base or trailing end secured to a one-way suture which has a series of exterior barbs providing for gripping of the flesh in one direction only, the barbs permitting movement of the suture through the flesh in the direction the needle is inserted, (b) pushing the needle to extend out of the flesh at a point laterally spaced from the wound, then gripping the needle from the point end and pulling the needle out of the flesh, leaving a trailing end of the suture in the open wound, (c) severing the suture from the needle, (d) repeating the procedure of step (a) at the opposite side of the open wound, at a position to form a suture pair of two sutures located across the wound from one another, (e) repeating steps (b) and (c) at said opposite side of the open wound, (f) repeating steps (a) through (e) to form additional suture pairs as necessary at further locations along the wound depending on the size of the wound, (g) bringing the two sides of the wound together, and (h) connecting together trailing ends of the two sutures of each suture pair to bind the wound in a closed position.

2. The method of claim 1, wherein the step of securing together trailing ends of the sutures comprises binding together the two trailing ends by means of heat fusion.

3. The method of claim 2, wherein the suture is formed of nylon.

4. The method of claim 1, wherein the suture is formed of nylon.

5. The method of claim 1, wherein the suture has said barbs oriented at progressively staggered positions around the periphery of the suture.

6. The method of claim 1, wherein the surgical needle is a detachable needle and wherein the step of severing the suture from the needle comprises, while conducting the step of pulling the needle out of the flesh, restraining the trailing end of the suture and pulling the needle with sufficient force to detach it from the suture at a position wherein the leading end of the suture is well below the surface of the flesh, thereby leaving the leading end of the suture within the flesh.

7. The method of claim 6, wherein the base end of the detachable needle has metric markings as a visual reference for a surgeon, and including the surgeon's predetermining the depth of needle-suture severing by detaching the needle at a desired depth by reference to the metric markings.

8. The method of claim 1, wherein the suture has a leading end region free of barbs, and wherein the step of pulling the needle out of the flesh comprises pulling the barb free leading end of the suture to the flesh, leaving the barbs well below the flesh so as to avoid downward tension at or near the surface of the skin.

9. A surgical method for bringing and holding together two tissue portions in a living patient or animal, to allow healing and regrowth together of the two tissue portions on either side of a tissue separation, comprising:

(a) at the tissue separation, inserting a surgical needle into tissue at one side of the separation, penetrating into the one tissue portion, the needle having a trailing end secured to a one-way suture which has a multiplicity of exterior barbs providing for gripping of the tissue in one direction only, the barbs permitting movement of the suture through the tissue in the direction the needle is inserted, the surgical needle being a part of a double-armed suture which includes first and second such surgical needles oriented in opposite directions and a single suture extending between the trailing ends of the two surgical needles, the suture having said exterior barbs oriented in one direction for a first portion of the length of the suture and in the opposite direction for a remaining, second portion of the length of the suture, each portion having the barbs oriented so as to allow movement of that portion of the suture through the tissue in the same direction in which the needle secured to that portion of the suture is inserted, (b) pushing the first surgical needle to extend along an intended line of support and then out of the tissue at a point spaced from the tissue separation, then gripping the needle from its point end and pulling the needle out of the tissue, leaving said second portion of the suture extending in the tissue separation, (c) repeating the procedure of step (a) at the opposite side of the open wound, using the second surgical needle, at a position located across the tissue separation from the position in which the first needle was inserted, (d) repeating step (b) at said opposite side of the tissue separation, to the extent that said second portion of the suture is drawn through tissue at said opposite side of the separation, with the second surgical needle, (e) bringing the two tissue portions together, while drawing one or both of the surgical needles outwardly from the wound until the two portions of the suture are located substantially in respective tissue portions at opposed sides of the separation and the suture is drawn substantially tight so as to bind the two tissue portions together in a substantially closed position, and (f) severing the suture from the two surgical needles.

10. The surgical method of claim 9, wherein the surgical needles are detachable needles, detachable from the suture with a prescribed pulling force, and wherein the step of severing the suture from the two surgical needles comprises, while conducting the step of pulling the needle out of the tissue, pulling each needle with sufficient force to detach it from the suture at a position wherein the trailing end of the needle is well below the surface of the tissue, thereby leaving the suture well below the surface of the tissue.

11. The surgical method of claim 10, wherein the two tissue portions comprise two sides of an open wound at the skin of a patient.

12. The surgical method of claim 9, wherein the suture is formed of nylon.

13. The surgical method of claim 9, wherein the suture is formed of a resorbable material.

14. The surgical method of claim 9, wherein the two tissue portions are portions of a tendon which is at least partially severed.

15. The surgical method of claim 9, wherein the two tissue portions comprise two sides of an open wound at the skin of a patient, wherein the suture includes leading end regions free of barbs, adjacent to the trailing end of each surgical needle, and including leaving the barb free regions of the suture just below the skin to avoid pulling in of the skin.

16. A surgical method for supporting skin and adjacent subcutaneous tissue of a patient in a facelift operation, comprising:
    selecting one or more paths through the patient's tissue on which lines of tissue support are desired,
    selecting a surgical needle of sufficient length to be inserted through a first of such selected paths in the tissue, the surgical needle having a trailing end secured to a one-way suture which has a multiplicity of exterior barbs providing for gripping of the tissue in one direction only, the barbs permitting movement of the suture through the tissue in the direction the needle is inserted,
    pushing the needle into the tissue, below the skin and along the selected path for the desired line of tissue support, until the needle extends out through the skin at a distal end of the selected path,
    gripping the needle from its point end and pulling the needle out of the patient's tissue, leaving the one-way suture lying within the tissue along the selected path,
    severing the suture from the surgical needle, at a point below the skin, leaving a leading end of the one-way suture hidden beneath the skin at said distal end of the selected path,
    as needed for the particular facelift operation, inserting a needle in additional selected paths for additional desired lines of tissue support, to place additional one-way sutures below the skin at said additional desired lines of tissue support,
    applying tension to the trailing end of each suture, to engage the barbs against the internal tissue along said one or more desired lines of tissue support, and securing the trailing end of each suture, in the tensioned condition, such that the desired line of support is placed in tension to provide the desired tissue support.

17. The surgical method of claim 16, wherein the trailing end of each suture is secured to tissue of the patient.

18. The surgical method of claim 16, wherein the trailing end of each suture is secured to a trailing end of another one-way suture which extends in essentially an opposite direction.

19. The surgical method of claim 16, wherein the surgical needle is a detachable needle which detaches from the suture under a prescribed degree of pulling force, and wherein the step of severing the sutures from the surgical needle comprises, while conducting the step of pulling the needle out of the tissue, restraining the trailing end of the suture and pulling the needle with sufficient force to detach it from the suture at a position wherein the trailing end of the needle is at a selected depth below the surface of the skin, thereby leaving the suture at said selected depth.

20. The surgical method of claim 19, wherein the surgical needle has near its trailing end metric markings as a visual reference for a surgeon, and including the surgeon's predetermining the depth of needle-suture severing by detaching the needle at a desired depth by reference to the metric markings.

21. A surgical method for bringing and holding together two tissue portions in a living patient, to allow healing and regrowth together of the two tissue portions on either side of a tissue separation, comprising:
    (a) at the tissue separation, inserting a surgical needle into tissue at one side of the separation, penetrating into the one tissue portion, the needle having a trailing end secured to a one-way suture which has a multiplicity of exterior barbs providing for gripping of the tissue in one direction only, the barbs permitting movement of the suture through the tissue in the direction the needle is inserted,
    (b) pushing the needle to extend along an intended line of support and then out of the tissue at a point spaced from the tissue separation, then gripping the needle from its point end and pulling the needle out of the tissue, leaving a trailing end of the suture in the tissue separation,
    (c) severing the suture from the needle,
    (d) repeating the procedure of step (a) at the opposite side of the tissue separation, in the other tissue portion, at a position to form a suture pair of two sutures located across the tissue separation from one another,
    (e) repeating steps (b) and (c) at said opposite side of the tissue separation, in said other tissue portion,
    (f) repeating steps (a) through (e) to form additional suture pairs as necessary at further locations in the tissue separation depending on the size of the tissue separation,
    (g) bringing the two tissue portions together, and
    (h) connecting together trailing ends of the two sutures of each suture pair to bind the tissue separation in a closed position to facilitate regrowth together of the two tissue portions.

22. The surgical method of claim 21, wherein the step of securing together trailing ends of the sutures comprises binding together the two trailing ends by means of heat fusion.

23. The surgical method of claim 21, wherein the two tissue portions comprise sections of a tendon of the patient.

24. The surgical method of claim 23, wherein the step of securing together trailing ends of the sutures comprises binding together the two trailing ends by means of heat fusion.

25. The surgical method of claim 21, wherein the two tissue portions comprise two sides of an open wound at the skin of a patient, and wherein the step of severing the sutures comprises severing the sutures below the skin surface.

26. The surgical method of claim 21, wherein the surgical needle is a detachable needle, detachable from the suture with a prescribed pulling force, and wherein the step of severing the suture from the surgical needle comprises, while conducting the step of pulling the needle out of the tissue, pulling the needle with sufficient force to detach it from the suture at a position wherein the trailing end of the needle is well below the surface of the tissue, thereby leaving the suture well below the surface of the tissue.

27. A surgical needle and suture combination, comprising:

a surgical needle, a one-way suture having a series of exterior barbs providing for gripping of tissue in one direction only, the barbs permitting movement of the suture through tissue in the direction the needle is inserted, a detachable connection means securing the trailing end of the needle to a leading end of the suture, for releasing the needle from the suture when the needle pulls the suture with a prescribed amount of tension, and the needle having near its trailing end metric markings as a visual reference indicating distance from the trailing end of the needle, whereby a surgeon can predetermine a depth at which the needle is released from the suture by reference to the markings.

* * * * *